(12) United States Patent
Lopez

(10) Patent No.: US 10,585,047 B2
(45) Date of Patent: Mar. 10, 2020

(54) METHOD AND SYSTEM OF CHECKING A FACILITY FOR THE OPTICAL INSPECTION OF GLASS CONTAINERS

(71) Applicant: TIAMA, Vourles (FR)

(72) Inventor: Bernard Lopez, Caluire et Cuire (FR)

(73) Assignee: TIAMA, Vourles (FR)

( * ) Notice: Subject to any disclaimer, the term of this patent is extended or adjusted under 35 U.S.C. 154(b) by 0 days.

(21) Appl. No.: 16/092,793

(22) PCT Filed: Apr. 11, 2017

(86) PCT No.: PCT/FR2017/050873
§ 371 (c)(1),
(2) Date: Oct. 11, 2018

(87) PCT Pub. No.: WO2017/178754
PCT Pub. Date: Oct. 19, 2017

(65) Prior Publication Data
US 2019/0145904 A1    May 16, 2019

(30) Foreign Application Priority Data

Apr. 15, 2016  (FR) .................................... 16 53360

(51) Int. Cl.
*G01N 21/00*       (2006.01)
*G01N 21/93*       (2006.01)
*G01N 21/90*       (2006.01)

(52) U.S. Cl.
CPC ............ *G01N 21/93* (2013.01); *G01N 21/90* (2013.01)

(58) Field of Classification Search
CPC ............... G01N 21/9054; G01N 21/90; G01N 2033/0081; G01N 21/9018; G01N 21/9036

USPC ....................................... 356/239.4
See application file for complete search history.

(56) References Cited

U.S. PATENT DOCUMENTS

| 6,122,042 A * | 9/2000 | Wunderman ............ A61B 1/05 |
| | | 356/343 |
| 6,466,691 B1 | 10/2002 | Heuft |
| 2003/0012421 A1 | 1/2003 | Werzinger |
| 2009/0316145 A1 | 12/2009 | Widera |

(Continued)

FOREIGN PATENT DOCUMENTS

| DE | 33 24 449 | 1/1985 |
| DE | 196 46 694 | 5/1998 |

(Continued)

*Primary Examiner* — Md M Rahman
(74) *Attorney, Agent, or Firm* — Clark & Brody

(57) ABSTRACT

The invention provides a method and a system of checking a procedure for the optical inspection of glass containers (12), characterized by a procedure for the optical recognition of a control mark (42) of a control container having optical properties of transformation spectral such that:

Figure 1:
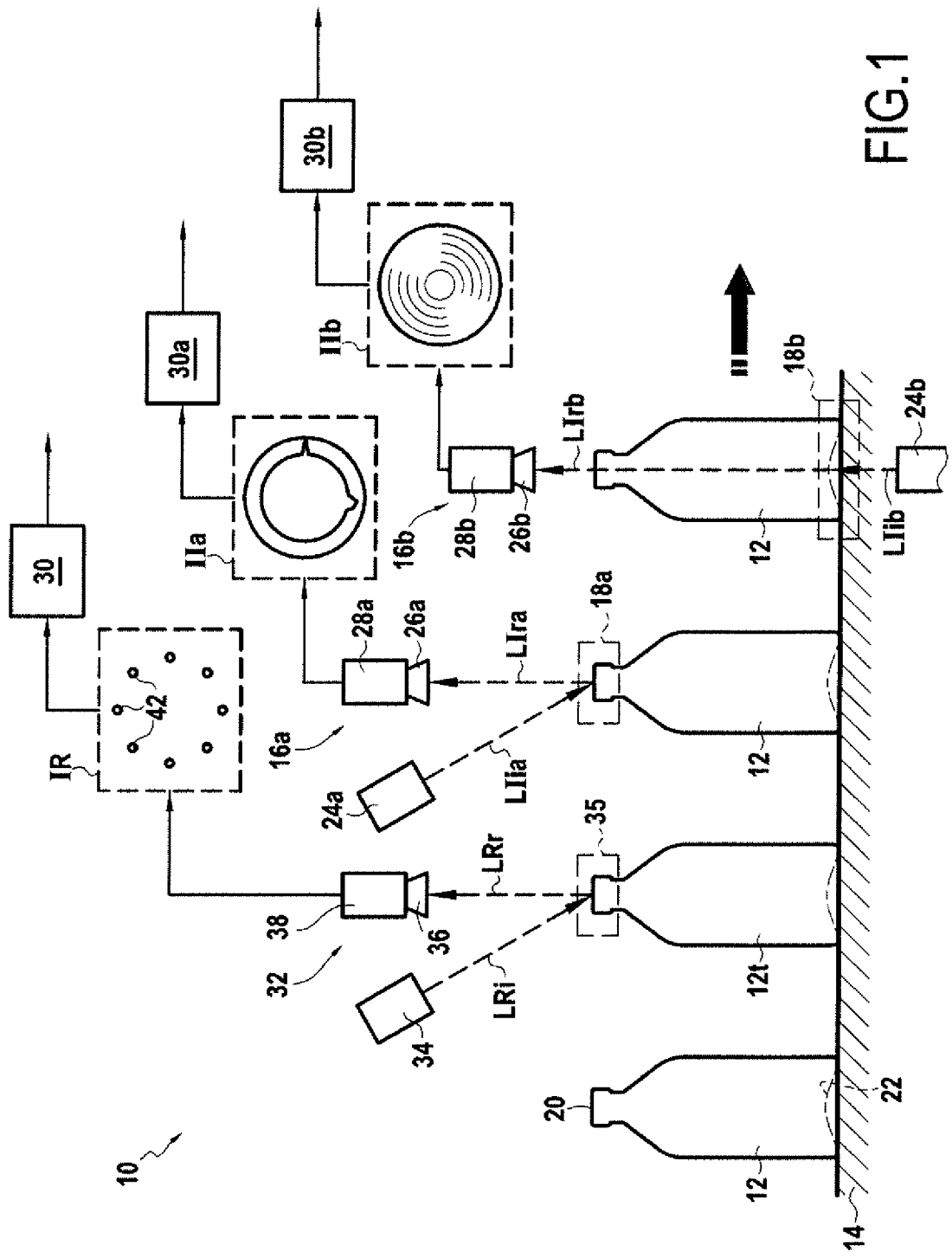

the transformation of the spectral intensity distribution between the incident (LRi) and return (LRr) recognition lights, by the mark (42), is different from that caused by interaction with a marking portion free of any mark (46);

the transformation of the spectral intensity distribution between the incident (LIi) and return (LIr) inspection lights, by the mark, is not different, inside at least one useful portion of the inspection spectral band (BSI), from that caused by interaction with a marking portion free of any mark (46).

17 Claims, 4 Drawing Sheets

(56) References Cited

U.S. PATENT DOCUMENTS

| | | | |
|---|---|---|---|
| 2010/0282560 A1 | 11/2010 | Voegtle et al. | |
| 2012/0059615 A1 | 3/2012 | Pschichholz | |
| 2012/0069170 A1* | 3/2012 | Gesley | G01N 21/6458 348/79 |
| 2016/0054234 A1 | 2/2016 | Niedermeier | |

FOREIGN PATENT DOCUMENTS

| | | |
|---|---|---|
| DE | 299 10 452 | 8/1999 |
| DE | 10 2010 043632 | 5/2012 |
| DE | 10 2011 084 453 | 4/2013 |
| DE | 10 2012 204 277 | 9/2013 |
| DE | 10 2015 203060 | 8/2016 |
| EP | 0 613 732 | 9/1994 |
| EP | 2 186 736 | 5/2010 |
| EP | 2 581 732 | 4/2013 |
| JP | 09-89805 | 4/1997 |
| JP | 2005-195496 | 7/2005 |
| WO | 2005/119224 | 12/2005 |

* cited by examiner

METHOD AND SYSTEM OF CHECKING A FACILITY FOR THE OPTICAL INSPECTION OF GLASS CONTAINERS

The invention relates to a method and a system of checking a facility for the optical inspection of glass containers.

In the manufacture of glass containers, notably bottles or jars, there is the possibility that one or more containers has/have a non-compliant physical characteristic, notably a geometric characteristic. This non-compliant characteristic may notably comprise one or more surface defects, such as wrinkles or crevices, or one or more internal defects in the material, such as cracks, inclusions, or bubbles, or even one or more dimensional defects in the container, e.g. regarding a diameter, a height, a glass thickness, a flatness of lip surface, etc.

For detecting the presence of such defects, it is known to provide, in the glass container manufacturing lines, facilities for the optical inspection of the containers which are capable of determining, by an optical procedure, an inspection result related to one or more characteristics of a container, and even of determining a normal or abnormal character thereof. In a manufacturing line, these optical inspection facilities may be associated with mechanisms for ejecting non-compliant containers.

However, such optical inspection facilities must be adjusted and calibrated and must, during operation, be checked in order to ensure that, over time and during the production of glass containers, the inspection carried out is always reliable.

A known method of checking an optical inspection facility is to manually submit a control container to this facility, so that it is inspected by the facility. The control container generally comprises at least one known defect likely to be detected by the inspection facility. It is then checked that the inspection facility has a nominal operation by checking that it correctly detects, through its optical inspection procedure, that the container has a defect.

Generally, optical inspection facilities are installed on a container conveyor line so as to automatically inspect all or in any case a significant part of the containers conveyed on the line. The optical inspection facilities are therefore installed on a conveying path of the containers. In order to be able to check the nominal operation of the optical inspection facility, it is therefore desirable to be able to perform the checking without interrupting the conveyor line, simply by inserting a control container in the conveying line, upstream of the inspection facility to be checked. In such a case, it is therefore necessary to be able to recognize the control container thus inserted in order to be able to check that this control container is correctly detected by the inspection facility as having a defect.

For this, it is known to provide a control mark on the control container making it possible recognize it. This control mark is generally added onto the control container after its manufacture, once an expected inspection result has been determined for this control container, e.g. related to a particular physical characteristic, notably a characteristic forming a defect.

This control mark is generally intended to be detected visually by an operator, which enables the operator to recognize and recover the control container at the exit from the machine. The operator checks the detection carried out by the machine. Usually provision is made for a specific mode of operation of the optical inspection facilities during the passage of control containers: in this "checking" mode, the results of the inspection are presented graphically to the operator, for example, for the operator to compare the inspection results of the control containers to the expected results. The inspection results of the control containers are not included in the current production statistics. It may also be provided, in some optical inspection facilities, that the control containers are specifically automatically ejected by the facility, e.g. by providing a recovery bin for the control containers. The task of checking, thus involving the operators, has several drawbacks: need to interrupt the flow, which disrupts operations, need to transfer the machine into checking mode, the verdict being monitored by the operator without the possibility of an automated digital report.

This control mark is generally intended to be detected visually by an operator, or in any case the control mark is optically visible. In this case, if the control mark is borne by the control container, on a marking portion thereof, the control mark must be affixed to a portion of the container which is not inspected by the optical inspection facility. Indeed, otherwise, the control mark would be detected as being a defect or, if it is affixed to a portion of the container comprising a defect, this defect might not be detected. As there may be several optical inspection facilities on the same line, intended to additionally check the entirety or a large part of the surface of the containers, it is not always possible to find an ideal location on the control containers capable of receiving the control mark.

It is also conceivable to provide the container with other types of recognition means, e.g. by affixing a mark recognizable by radio-frequency interrogation, e.g. with an RFID chip. However, the recognition of such a chip uses electromagnetic waves outside the optical domain, requiring the mastery of other technologies. In addition, such RFID chips have a significant cost and they hinder optical inspection, so that it is not always possible to find an ideal location on the control containers capable of receiving the control mark in the case of a complete or nearly complete check of the containers.

Document WO-2005/119224 describes an apparatus including a conveyor loop for the test containers. The loop is connected, at one end, to the checking path upstream of the inspection devices, and at its other end, to the transport path downstream of the inspection devices. A controller preferably automates a test cycle for providing test containers in the inspection route, receiving information regarding the characteristics detected in the test containers, and ensuring the return of the test containers from the checking path to the conveyor loop for the test containers. The checking procedure requires stopping the conveyor flow of the articles to allow the passage of the test containers which are then recovered and stored on a waiting conveyor to then allow the recirculation of the production containers. This disrupts and notably slows the rate of inspection. In addition, the storage line necessary represents a space requirement problem. It is noted that there is no means of recognizing the samples. Thus, checking requires transferring the facility, and therefore the portion of the manufacturing line in which it is inserted, into a particular test mode, incompatible with continuing the inspection of the containers in production. Furthermore, the only means of associating the test containers with the defects that they bear is to classify them and keep their order of passage, which presents a major risk of error.

The purpose of the invention is therefore to provide a new method and a new system of checking an optical inspection facility based on optical procedures in the optical domain and making it possible to automatically recognize the passage of control containers in the optical inspection facility.

For this purpose, the invention provides a method of checking a procedure for the optical inspection of glass containers, in which the procedure for the optical inspection of a container comprises the steps of:
illuminating at least one inspected portion of the container with an incident inspection light having an incident inspection spectrum;
collecting a return inspection light resulting from the interaction of the incident Inspection light with the inspected portion of the container, the return inspection light having a return inspection spectrum;
converting, in an inspection spectral band, the collected return inspection light into a linear or two-dimensional multipoint inspection digital image;
analyzing the inspection digital image for determining an inspection result from the inspected container;
wherein the method of checking comprises the steps of:
Inspecting, in accordance with the optical inspection procedure, a control container comprising a control mark affixed to a marking portion of the control container;
comparing an inspection result from the control container determined by the optical inspection procedure to a known inspection result from the control container.

The method of checking comprises a procedure for the optical recognition of a control container by optical reading of a control mark in a marked marking portion of the control container, comprising the steps of:
illuminating at least the marking portion of the container with an incident recognition light having an incident recognition spectrum;
collecting a return recognition light resulting from the interaction of the incident recognition light with the marking portion and a possible control mark, the return recognition light having a return recognition spectrum;
converting, in a recognition spectral band, the collected return recognition light into a linear or two-dimensional multipoint recognition digital image;
analyzing the recognition digital image by computer for recognizing the possible control mark therein.

The invention also relates to a system of checking a facility for the optical inspection of glass containers, wherein the container inspection facility comprises:
a source of incident inspection light illuminating an inspection area of the facility and having an incident inspection spectrum;
an optical collector collecting a return inspection light resulting from the interaction of the incident inspection light with an inspected portion of a container placed in the inspection area, the return inspection light having a return inspection spectrum;
an inspection photoelectric sensor converting, in an inspection spectral band, the collected return inspection light into a linear or two-dimensional multipoint inspection digital image;
a computer unit for analyzing the inspection digital image configured for determining an inspection result from the inspected container.

The system of checking comprises:
at least one control container comprising a control mark affixed to a marking portion of the control container, the container being suitable for being positioned in the inspection area of the optical inspection facility, and;
a computer processing unit configured for comparing an inspection result from a control container, as determined by the optical inspection facility, to an expected inspection result from the control container.

The system comprises a facility for the optical recognition of a control container by optical recognition of a control mark in a marking portion of the control container, comprising:
a source of incident recognition light illuminating a recognition area of the facility and having an incident recognition spectrum;
an optical collector collecting, in the presence of a control container in the recognition area, a return recognition light resulting from the interaction of the incident recognition light with the marking portion and with a possible control mark, the return recognition light having a return recognition spectrum;
a recognition photoelectric sensor converting, in a recognition spectral band, the collected return recognition light into a linear or two-dimensional multipoint recognition digital image;
a computer unit for analyzing the recognition digital image for detecting the possible control mark.

In a particular embodiment, the method and/or the procedure are characterized in that the control mark comprises a photoluminescent material which, under the effect of an illumination in an excitation spectral band, emits a luminescence light which exhibits a luminescence spectrum, and in that the incident recognition spectrum comprises at least one part of the excitation spectral band while the incident inspection spectrum is disjoint from the excitation spectral band.

In another particular embodiment, which may be combined with the previous one, the method and/or the procedure are characterized in that the control mark comprises a photoluminescent material which, under the effect of an illumination in an excitation spectral band, emits a luminescence light which exhibits a luminescence spectrum, and in that the luminescence spectrum is within the recognition spectral band and disjoint from the inspection spectral band.

In these examples, the excitation spectral band of the luminescent material may have a maximum wavelength less than 400 nm while the incident inspection spectrum may have a minimum wavelength greater than 400 nm.

More generally, the control mark, affixed to the marking portion of a control container, has optical properties of spectral transformation such that:
the transformation of the spectral intensity distribution between the incident recognition light and the return recognition light, caused by interaction with the marked marking portion, is different, inside at least the recognition spectral band, from a transformation of the spectral intensity distribution between the incident recognition light and the return recognition light, caused by interaction with a marking portion free of any mark;
the transformation of the spectral intensity distribution between the incident inspection light and the return inspection light, caused by interaction with the marked marking portion, is not different, inside at least one useful portion of the inspection spectral band, from the transformation of the spectral intensity distribution between the incident inspection light and the return inspection light by interaction with a marking portion free of any mark.

In general, the control mark, affixed to the marking portion of a control container, has optical properties of spectral transformation which confer on the marked marking portion optical properties of spectral transformation which differ from those of the marking portion free of any mark in a useful portion of the incident recognition spectrum and/or of the recognition spectral band and which are identical to those of the marking portion free of any mark in at least the whole of a useful portion of the incident inspection spectrum and of the inspection spectral band.

According to optional features, taken alone or in combination:

- The optical properties of spectral transformation of the marked marking portion may differ from those of the free marking portion in a part of the incident recognition spectrum that is not included in the incident inspection spectrum;
- The optical properties of spectral transformation of the marked marking portion may differ from those of the free marking portion so that, when they are illuminated by the incident recognition light, the corresponding return recognition lights for the marked marking portion and for the free marking portion are different in the recognition spectral band;
- The optical properties of spectral transformation of the control mark may be such that, when they are illuminated by the incident inspection light, the return inspection light for the marked marking portion and the return inspection light for the free marking portion are identical in the useful portion of the inspection spectral band;
- The Interaction of the inspection light with the marked marking portion and with the free marking portion may cause the same neutral or modifying transformation, between the spectral intensity distribution of the incident inspection light and the spectral intensity distribution of the return inspection light in the inspection spectral band;
- The inspection spectral band and the recognition spectral band may be disjoint, and the return inspection spectrum and the return recognition spectrum may be disjoint;
- The Incident inspection spectrum and the incident recognition spectrum may be disjoint;
- The control mark may absorb a control spectral band which is included in the recognition spectral band and which is not included in the inspection spectral band;
- The control mark may absorb a control spectral band which is included in the incident recognition light and which is not included in the incident inspection light;
- The recognition procedure may identify the control container as belonging to a determined category of control containers among a plurality of distinct categories of control containers;
- The recognition procedure may uniquely identify the control container. For this, the control mark may comprise an identifier making it possible to uniquely identify the control container;
- The recognition procedure may identify the control container as belonging to a determined category of control containers, associated with the same expected inspection result. For this, the control mark may comprise an identifier making it possible to identify the control container as belonging to a determined category of control containers, associated with a same expected inspection result;
- The marking portion of a control container may at least partly intersect the inspected portion of the control container that is inspected in the inspection procedure;
- The method may comprise the step of inserting at least one control container having an expected inspection result into a series of containers to be inspected and checking that the inspection procedure determines the expected inspection result for said control container;
- In the system, the recognition area and the inspection area may be disjoint or at least partly coincide;
- The recognition and inspection light sources may be switched on alternately;
- The inspection photoelectric sensor and the recognition photoelectric sensor may be distinct sensors;
- The control mark may be affixed to a marking portion of the control container which is included in the inspected portion of the container that is inspected by the inspection facility;
- The identifier of the control mark may at least partly consist of a pattern of the control mark;
- The computer processing unit may comprise a means of storing the correspondence relationships between identifiers of control marks and expected inspection results for control containers bearing said identifiers.

Various other features emerge from the description below made with reference to the appended drawings, which depict embodiments of the object of the invention by way of non-restrictive examples.

FIG. 1 schematically illustrates a container transport line including an optical inspection facility and a system of checking in conformity with the invention.

Figure 2A:
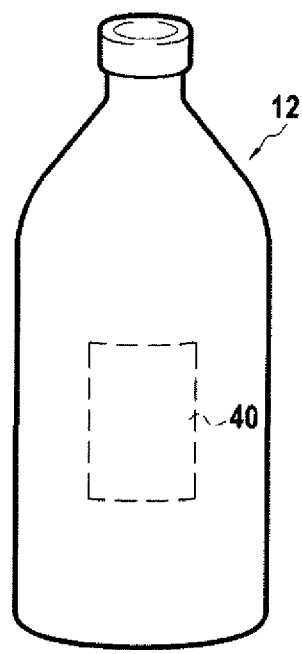
Figure 2B:
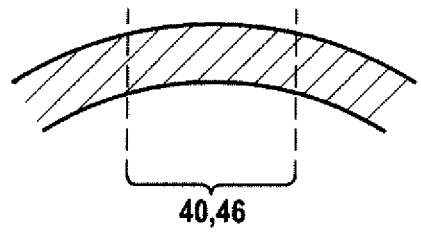

FIGS. 2A and 2B respectively illustrate a standard container and a cross-section of its marking portion.

Figure 2C:
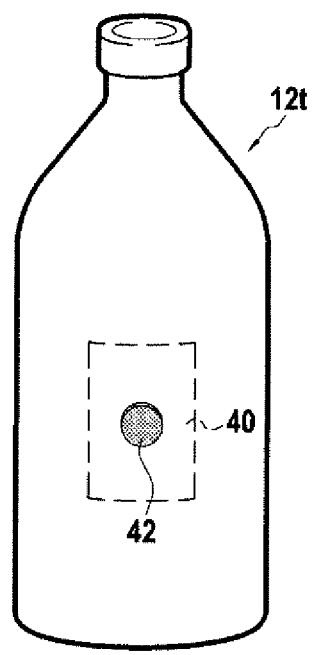
Figure 2D:
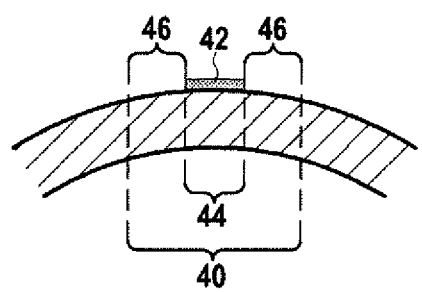

FIGS. 2C and 2D respectively illustrate a control container to which a control mark is affixed, and a cross-section of its marking portion.

Figure 3A:
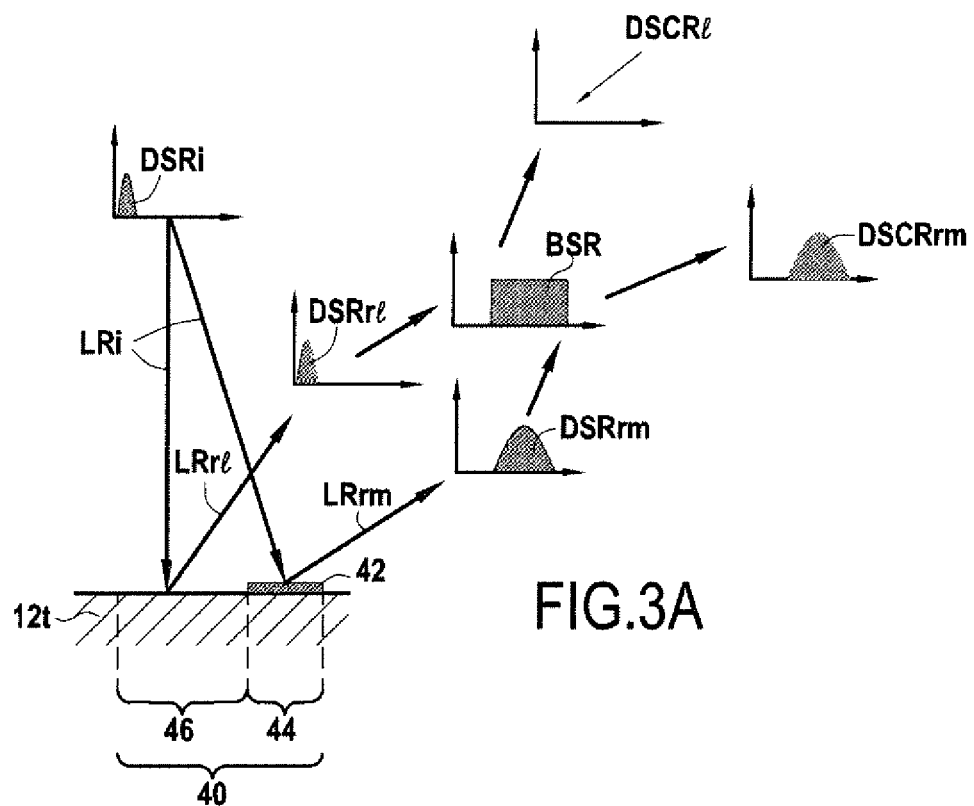
Figure 3B:
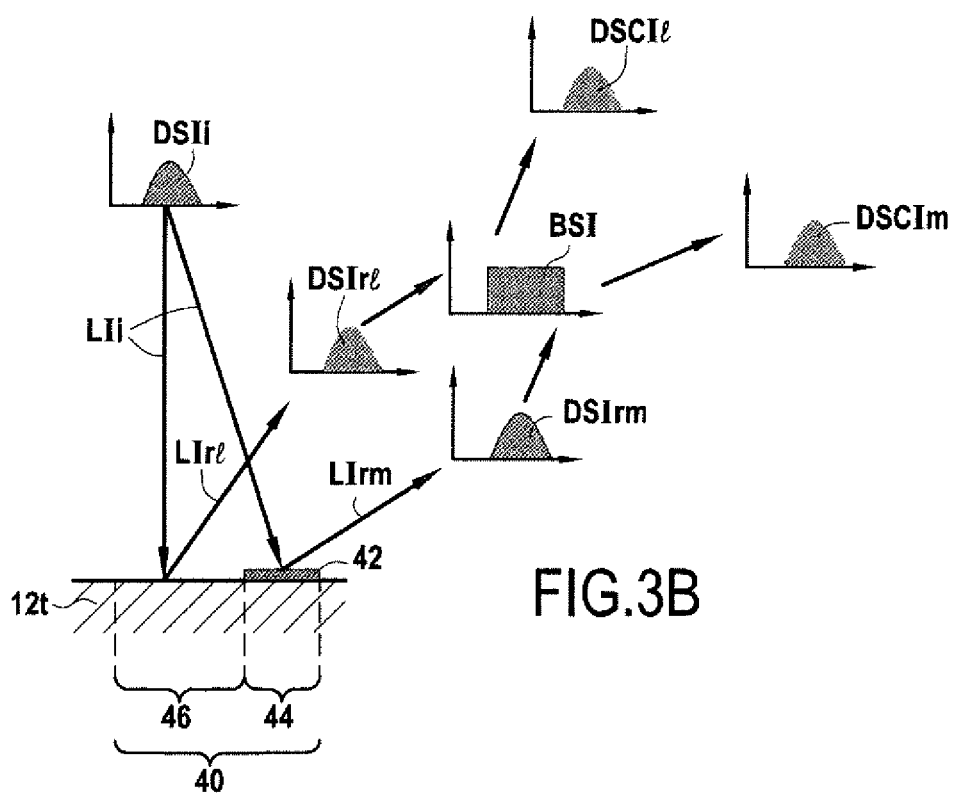

FIGS. 3A and 3B respectively illustrate a recognition procedure and an inspection procedure for an embodiment of the invention.

Figure 4A:
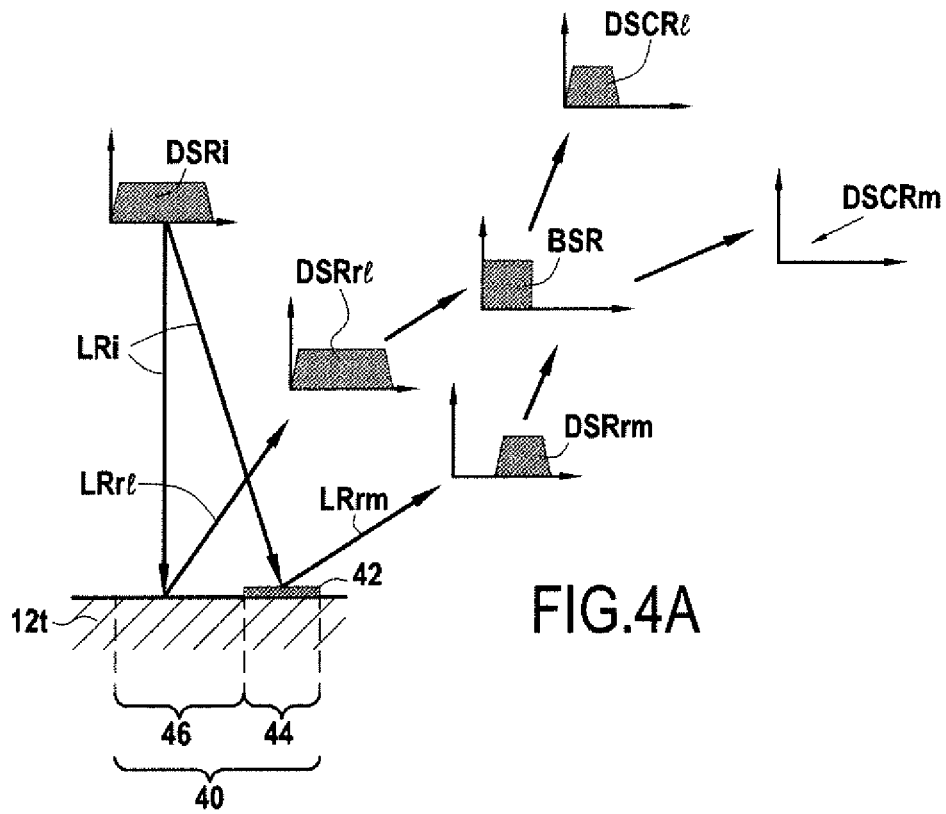
Figure 4B:
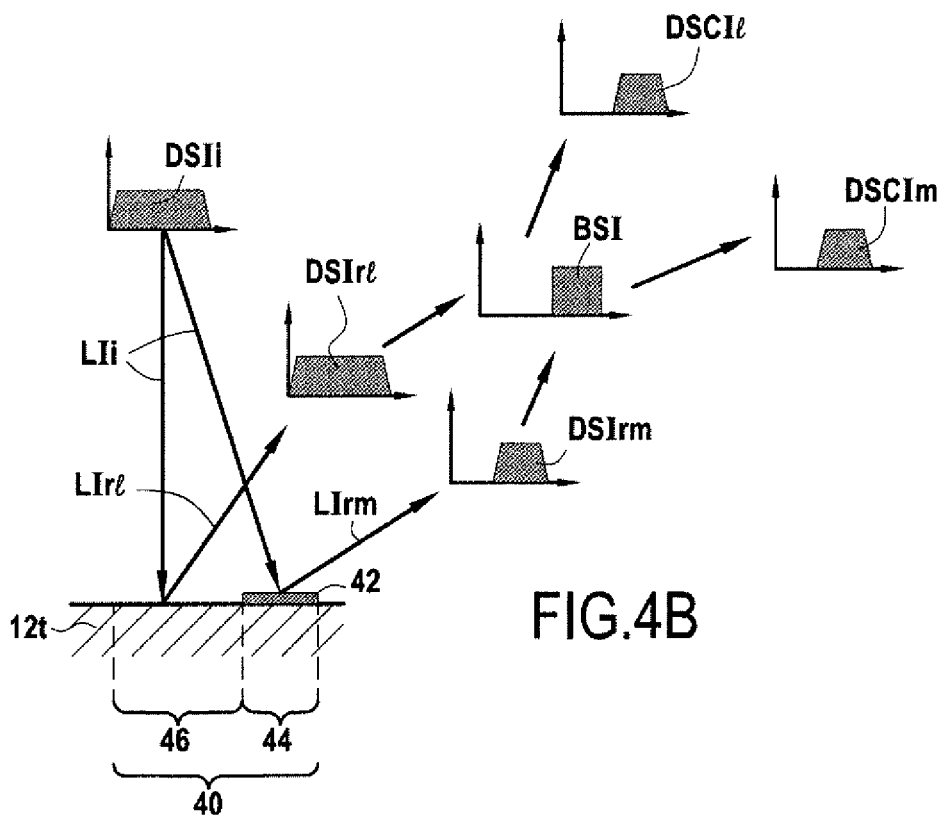

FIGS. 4A and 4B respectively illustrate a recognition procedure and an inspection procedure for a second embodiment of the invention.

The invention relates to the field of optical inspection facilities and optical inspection procedures for glass containers, notably bottles or jars.

Glass is a silicon oxide-based (e.g. SiO2-, silica-based) amorphous material possibly comprising fluxes and, for example, metal oxides such as boron trioxides, alkaline oxides (such as calcium or magnesium oxides, sodium oxides, etc.). The most common glass for containers ("bottle glass") is a soda-lime glass. A wide variety of colors is offered. Apart from exceptionally dark colors, the glass bottle is generally transparent to visible light, at least in one part of the visible domain, which allows the consumer to see the contained product. This transparency may be used by optical procedures and facilities for inspecting containers operating transparently, by transmission of a light through the material of the container. Indeed automatic glass container inspection methods are very frequently optical procedures, and notably use industrial vision technologies.

These optical inspection facilities and optical inspection procedures are capable of determining an inspection result for a given container. This inspection result may be linked to, or consist of, the detection or the determination of at least one physical characteristic of a container, notably a geometric characteristic, e.g. with a view to determining whether a container is compliant or non-compliant with respect to an admissible standard. This characteristic may notably include the presence and/or the size or the geometry of a surface defect, such as wrinkles or crevices, and/or a fault internal to the material, such as cracks, inclusions, or bubbles. This characteristic may include the number, the density, the location or the distribution of such defects. This characteristic may further include one or more dimensions of the containers, relating, for example, to a diameter, a height, a glass thickness, a flatness of surface, a circularity etc. It may further include a combination of the different elements referred to or mentioned above.

More particularly, these optical inspection facilities and optical inspection procedures are capable of operating on line, i.e. capable of operating in a line in which a flow of containers is circulating following each other by being moved by a conveyor or handling system, notably a manufacturing, transport, filling, processing and/or packaging line of glass containers, etc. The containers in the flow may be moved from station to station to be inspected in at least one inspection facility, or even in different successive inspection facilities. In an inspection facility, according to the method of inspection, the containers may be immobilized, remain in continuous translation or undergo rotations about an axis. The procedures and facilities are capable of automatically inspecting all the containers in the flow or at least a part of the containers in the flow on this line, this part of the containers in the flow preferably comprising at least one container selected at regular intervals in the flow.

FIG. 1 illustrates by way of example a transport line 10 of bottles 12 comprising a conveyor 14 that moves the bottles along a conveying path.

The line 10 comprises one or more inspection facilities, e.g. two inspection facilities 16a, 16b in the example of FIG. 1.

Furthermore, provision is made for an optical recognition procedure of a control container 12t by optical reading of a control mark borne by the control container, this procedure being implemented by an optical recognition facility 32.

These facilities 16a, 16b, 32 and the optical inspection and recognition procedures that they implement, operate exclusively in the optical domain covering the electromagnetic waves in the ultraviolet, visible and infrared domains, with a wavelength between 10 nm and 5 mm, preferably between 100 nm and 20 microns. Preferably, each procedure and optical facility operates in only one part of the optical domain. Of course, the line may, in addition, comprise inspection facilities operating according to a different, non-optical mode, e.g. according to a mechanical mode.

An optical inspection procedure of a container may comprise different steps, some of which may be simultaneous.

In an optical inspection procedure, at least one inspected portion of the container may be illuminated with an incident inspection light $LIi_a$, $LIi_b$ having an incident inspection spectrum. The inspected portion of the container consists of the portion of the container that the procedure may inspect and for which the procedure may determine an inspection result, e.g. through the ability to detect a physical characteristic sought from this container. This inspected portion may, in the case of a bottle, include all or part of the ring, the annular surface of the lip, the neck, the shoulder, the barrel, the bottom rim, the base, etc. or a combination of these parts of the bottle. In the example of FIG. 1, a first inspection facility 16a is intended to inspect the annular lip surface 20 of the bottle, while the second inspection facility 16b is intended to inspect at least one part of the base 22 of the bottle.

The illumination of the inspected portion may be performed using a source 24a, 24b of incident inspection light $LIi_a$, $LIi_b$ Illuminating an inspection area of the facility 18a, 18b.

The inspection area of the facility corresponds to the portion of space in the facility in which it is necessary to position the inspected portion of a container so that it is actually inspected by the facility. In the example of FIG. 1, the different inspection facilities have disjoint inspection areas 18a, 18b, i.e. which do not intersect, firstly since the two inspection facilities are provided for inspecting different portions of the container (in this case the ring surface 20 and the base 22 of a bottle type container respectively), and secondly because the inspection facilities are staggered on the line so that the inspection areas 18a, 18b correspond to different positions of the container along the conveying path, i.e. to different stations. However, it could be provided that two inspection facilities inspect the same inspected portion of the containers, and/or that two inspection facilities are arranged in the same position on the line, so that the inspection areas, whether or not disjoint, may correspond to the same position of the container along the conveying path, i.e. to the same station.

The source 24a, 24b of incident inspection light $LIi_a$, $LIi_b$ may be any source emitting radiation in the optical domain. It may include the ambient light around the facility and/or a dedicated source. A dedicated source may comprise multiple elementary, identical or non-identical sources. It may include one or more source(s) of uniform light, diffuse light, directional light, extended and/or point light, etc.

The optical inspection procedure may collect a return inspection light $LIr_a$, $LIr_b$ resulting from the interaction of the incident inspection light $LIi_a$, $LIi_b$ with the inspected portion of the container, the return inspection light having a return inspection spectrum.

The interaction of the incident inspection light $LIi_a$, $LIi_b$ with the inspected portion of the container, which results in the return inspection light $LIr_a$, $LIr_b$, may include an interaction by reflection on a surface of the inspected portion (as in the case of the first inspection facility 16a of FIG. 1), an interaction by a transmission through the constituent material of the inspected portion of the container (as in the case of the second inspection facility 16b of FIG. 1), or a combination of transmission and reflection. In the course of this interaction, the light may undergo various modifications by refraction, diffraction, reflection, spectrum modification, diffusion, etc., which transform the incident inspection light $LIi_a$, $LIi_b$, producing a return inspection light $LIr_a$, $LIr_b$.

For collecting a return inspection light $LIr_a$, $LIr_b$, the inspection facility may optionally include an optical collector collecting the return inspection light resulting from the interaction of the incident inspection light with the inspected portion of a container placed in the inspection area of the facility. In the illustrated example, the optical collector comprises an objective 26a, 26b belonging to an inspection camera 28a, 28b. In the present text, an optical collector may comprise an association of objectives or other optical elements including, for example, one or more from among lenses, optical mirrors, partially reflective strips, prisms, optical fibers, diaphragms or pinholes, etc.

In the present text, the spectrum of an incident or return light, is understood to mean all the wavelengths contained in this light, therefore for which the intensity of the light is not zero. The spectrum may be a continuous spectrum, may comprise multiple disjoint continuous portions and/or may comprise discrete rays. In the present text, two sets of wavelengths are disjoint if they do not include a common wavelength.

The optical inspection procedure may convert, in an inspection spectral band, the collected return inspection light into a linear or two-dimensional multipoint inspection digital image $Ii_a$, $Ii_b$. The inspection spectral band is the set of wavelengths of a light that may be converted into an inspection digital image. This is a feature of the conversion, and optionally of the collection of the return light, and notably of the means implemented for ensuring this conversion, and optionally of the means implemented for this collection. The inspection spectral band may include the entirety of the return inspection spectrum, in which case the entirety of the light information contained in the return inspection light is converted into the inspection image. The inspection spectral band may only include a part of the return inspection spectrum, in which case only the light information contained in this part of the return inspection spectrum is used for forming the inspection digital image. Conversely, the return inspection spectrum may only include a part of the inspection spectral band.

In the present text, a spectral band is understood to mean a set of wavelengths. This set is preferably continuous between two end wavelengths, but may comprise multiple disjoint continuous portions and/or may comprise discrete wavelengths.

In this text, the spectral intensity distribution of a light is the set of relative intensity values for each wavelength component of a light.

Typically, for this conversion operation, a linear or two-dimensional inspection photoelectric sensor is used, e.g. the sensor of an inspection camera $28a$, $28b$. Typically, the optical collector forms, on a sensitive surface of the photoelectric sensor, the stigmatic optical image of the inspected portion of the container. The sensitive surface of the photoelectric sensor comprises, for example, one or more series of juxtaposed photoelectric elements, in the case of a two-dimensional sensor, using a grid with perpendicular rows and columns. The inspection photoelectric sensor converts, in the inspection spectral band, the collected return inspection light into a linear or two-dimensional multipoint inspection digital image $II_a$, $II_b$, composed of pixels. The inspection digital image $II_a$, $II_b$ then corresponds to the stigmatic optical image of the inspected portion of the container which is formed on the sensitive surface of the inspection sensor by the inspection light collector.

The inspection spectral band in the text designates the spectral response of the inspection sensor, i.e. the wavelength range for which the sensor delivers, beyond a minimum detection threshold, a higher signal to noise. For example, some sensors are sensitive only to radiation in the visible domain, which is defined in this text as consisting of the electromagnetic wave spectrum in a wavelength range between 400 and 780 nanometers, others are sensitive in an infrared domain, e.g. over a wavelength range between 780 and 1400 nanometers, either exclusively over this infrared domain, or both over this infrared domain and over all or part of the visible domain. The inspection spectral band may also be adjusted by the presence of spectral filters interposed on the route of the return inspection light, e.g. in the optical collector, including filters consisting of materials or coatings implemented for producing the optical elements of this collector. The inspection spectral band is therefore a feature of the sensor and of the inspection collector. In the embodiment, it is therefore a feature of the inspection camera $28a$, $28b$.

In the present text, a photoelectric sensor may, for example, be a CCD, tri-CCD or CMOS technology sensor, comprising at least one network of photosites, i.e. of photosensitive elements such as photodiodes, or bolometers.

Preferably the inspection digital image $II_a$, $II_b$ comprises at least 128 pixels.

The procedure may optionally produce a unique inspection digital image $II_a$, $II_b$ for a given container and for a given inspection performed by a given optical inspection facility.

However, generally, in the sense of the present text, a digital image may include a series of digital images of a given container taken by the same optical facility. For example, a series of digital images of a given container, formed by the optical facility may comprise a series of digital images acquired at a rate of 10 images per second.

In a manner known to the person skilled in the art, the optical inspection procedure involves analyzing the inspection digital image $II_a$, $II_b$ for determining an inspection result, e.g. related to the detection or the determination of at least one physical characteristic of the inspected container. These techniques known to the person skilled in the art are not described here in detail.

In the present text, in the case where the digital image includes a series of digital images of a given container, the analysis may include the analysis of a single one of these images and/or of a plurality of these images and/or a combination or a transformation of these images. The analysis generally includes a step of segmentation, for separating objects (in this case a container or a specific physical characteristic of this container) with respect to a background of the image, then these objects are analyzed or measured in order to determine the photometric, morphological or geometric characteristics thereof. For detecting an object in an image, a photometric property of the object (or of the set of the image pixels of the object) is therefore used in the digital image (intensity, color or grayscale or their derivative or their distribution) which distinguishes it from the background on which the object appears (or of the set of the pixels of the background image on which the object appears) with sufficient contrast.

The analysis of inspection digital images is generally computerized using a computer unit 30 configured for determining the inspection result, e.g. a physical characteristic of the inspected container. The physical characteristic is, of course, that which has to be inspected by the optical inspection procedure or a characteristic that is directly related thereto.

In the present text, a computer unit may notably include in a known manner a microprocessor, data input/output buses, memory, connections to a computer network and/or a display. The computer unit 30 may be a computer unit 30a, 30b dedicated to an optical inspection or recognition facility, or may be shared between a plurality of optical facilities. The computer unit 30 may further be shared with other elements of the line 10. It may be, for example, a centralized unit for controlling the line or a part thereof. The computer unit 30 may be a virtual unit composed of all or part of a plurality of networked physical computer units.

The computer analysis of digital images produces an inspection result which may include a binary result (true/false, present/absent, compliant/non-compliant, etc.) and/or a qualitative, or even quantitative result, e.g. in the form of one or more measurements.

A method of checking an optical inspection procedure and a system of checking an optical inspection facility are provided. The method of checking preferably comprises a step consisting of inspecting a control container, in accordance with the optical inspection procedure, therefore, for example, with the aid of the optical inspection facility.

Then, provision may be made for comparing, preferably by computer, an inspection result from the control container determined by the optical inspection procedure, to an expected inspection result from the control container. This comparison, if it is done by computer, may be performed by the computer unit 30, or by another computer unit.

The correct operation of the procedure and facility may thus be checked by this comparison.

The method of checking may, for example, comprise the step of inserting at least one control container having an expected inspection result, e.g. due to the presence in the control container of a known physical characteristic, into a series of containers to be inspected, and checking that the inspection procedure determines the expected inspection result for the control container.

For this, as can be seen more particularly in FIGS. 2C and 2D, at least one control container 12*t* is provided comprising a control mark 42 affixed to a marking portion 40 of the control container 12*t*. The marking portion 40 is a portion of the container that is intended to bear the control mark 42. By comparison, a corresponding standard container 12, illustrated in FIGS. 2A and 2B, does not have any control mark on the marking portion 40, namely on its portion corresponding to the marking portion 40 of the control container 12*t*. The marking portion may, in the case of a bottle, include all or part of the ring, the annular surface of the lip, the neck, the shoulder, the barrel, the bottom rim, the base, etc., or a combination of these parts of the bottle.

The marked marking portion 44 is the part of said marking portion that is actually covered by the control mark 42 after the control mark 42 is affixed. It is therefore formed by the superimposition of the material of the container and the material of the control mark 42.

The mark 42 has a shape, the geometry of which is preferably defined and may comprise a pattern or a set of geometric patterns, optionally capable of encoding an identifier. The marking portion 40 is not necessarily entirely covered by the control mark 42 when the mark is affixed thereto.

A marking portion free of any mark, known as the free marking portion 46, therefore designates either a marking portion totally lacking in any control mark, in the case of a standard container 12 as illustrated in FIGS. 2A and 2B, or the space in the marking portion 40 which is not covered by the control mark 42 when the affixed control mark does not entirely cover it, as in the case of the control container 12*t* illustrated in FIGS. 2C and 2D. This is generally the case when the mark comprises an identifier pattern.

The control container 12*t* is a container for which an expected inspection result is known, e.g. due to the presence in the control container of at least one known particular physical characteristic. This physical characteristic is, for example, one of those mentioned above.

The known characteristic is preferably that or the one of those that is determined by the optical inspection procedure considered. It may be its reverse.

The expected result from the control container may have been determined by the inspection procedure that is to be checked or by any other automatic or manual procedure, by the facility that is to be checked or by another facility. It may have been determined or confirmed or completed by an operator, visually or otherwise, with or without a tool.

The control container is preferably a container which, except for one or more known particular physical characteristic(s), is identical to a standard container in the flow of containers circulating normally on the line. The present invention is applicable to a facility and/or a line on which multiple types of products circulate, in other words different types of standard containers, notably using different types of control containers similar to the different types of standard containers.

A standard container thus has a marking portion entirely free of any mark, while a control container thus has a marking portion marked by the presence of the control mark. For a given control container, the free marking portion is the marking portion before the control mark has been affixed or the part of this marking portion that is left free when the mark only partially covers the marking portion.

The control mark is preferably a mark that is affixed to the container after its manufacture.

The control mark is preferably affixed to a surface of the marking portion of the container, preferably on an outer surface of the marking portion.

Preferably, for the embodiments in which the inspection procedure comprises a transmission through the marking portion, the control mark is produced so as to have no impact on the path of a light ray, at least in the inspection spectral band.

The control mark comprises, for example, a thin layer of marking or printing material, preferably of a constant thickness, on a surface of the marking portion of the control container. In some embodiments, the thickness of the layer may be less than a micrometer. The control mark may consist, for example, of an ink and/or a varnish and/or a paint.

Of course, the container and the facility are adapted so that the container may be positioned in the inspection area of the optical inspection facility. The control mark is affixed to a marking portion of the control container which may be included in the inspected portion of the container that is inspected by the inspection facility.

The control mark may comprise a pattern (which may also be a set of geometric patterns), capable of encoding an identifier making it possible to uniquely identify the control container, e.g. like a serial number. Alternatively, the pattern of the control mark may comprise an identifier making it possible to identify the control container as belonging to a determined category of control containers, associated with the same expected inspection result, and/or with the same known physical characteristic, from among a plurality of control containers, each associated with the same inspection result, and/or with at least one distinct known physical characteristic for each category. In both cases, the control mark may comprise, as an identifier, a number written in the form of directly readable characters, e.g. In Arabic numerals or in Roman numerals, or in the form of a code, e.g. a bar code or a DataMatrix code or the like, or else in the form of a geometric code, the geometry of the marking being capable of being used as an identifier. In the example illustrated in FIG. 1, the control mark 42 comprises a series of circular dots arranged in an arc of a circle on the annular lip surface of a control container 12*t*. Such a mark may comprise an identifier that is deduced, for example, from the number and/or from the relative spacing of the dots of the mark 42. In this example, the surface of the lip forms the marking portion, and it should be noted that if the facility is an inspection of the surface of the lip, then this portion is also the inspected portion.

Alternatively the control mark may be a simple indicator that the container is a control container, without being associated with a particular physical characteristic. In such a case, the control mark may be a simple spot or block, the size and geometry of which will be just chosen for ensuring good detectability by the recognition procedure and facility.

An optical recognition procedure of a control container 12t may comprise various steps, some of which may be simultaneous.

In an optical recognition procedure, at least the marking portion of the container may be illuminated with an incident recognition light LRi having an incident recognition spectrum. The portion of the container that is illuminated may be wider than the marking portion if there is uncertainty about the exact position of the marking portion. It may therefore be a wider expected marking position, which may optionally cover a large part of the container. In the example of FIG. 1, the recognition facility 32 is intended to recognize a mark affixed to the annular lip surface 20 of a container, this surface therefore being the expected marking portion. It is noted therefore that, in this embodiment, the marking portion of a control container 12t coincides at least partly with the inspected portion of this control container 12t when it is inspected by at least one of the two inspection facilities.

The illumination of the marking portion may be performed using a source 34 of incident recognition light illuminating a recognition area 35 of the facility and having an incident recognition spectrum.

The recognition area 35 of the facility corresponds to the portion of space in which it is necessary to position the marking portion of a container so that the control mark may be actually recognized by the facility. In the example of FIG. 1, the recognition facility 32 is separate from the inspection facilities 16a, 16b. Thus, the recognition area 35 is physically disjoint from the inspection area 18a, 18b, here of the two inspection facilities. The recognition area 35 corresponds, with respect to the inspection area 18a, 18b, to different positions of the container along the conveying path. However, provision could be made, at least in some cases, that a recognition area may at least partly coincide, or even does coincide, with an inspection area, notably in the case where the marking portion of a container at least partly coincides with the inspected portion of this container. More generally, at least in some cases, it could be provided that an inspection facility and a recognition facility, while respectively inspecting an inspected portion and a marking portion of a container which would possibly be disjoint, are arranged in the same position on the line, such that the inspection and recognition areas, while optionally being disjoint, would correspond to the same position of the container along the conveying path, and therefore to the same station.

Different types of sources 34 of incident recognition light LRi may be implemented, every source 34 of incident recognition light emitting radiation in the optical domain. The source of incident recognition light preferably includes a dedicated source, which may optionally comprise a plurality of elementary identical or non-identical sources. It may include one or more source(s) of uniform light, diffuse light, directional, extended and/or point light, etc.

The optical recognition procedure may collect a return recognition light LRr resulting from the interaction of the incident recognition light LRi with the marking portion of the container, and with a possible control mark on this marking portion, the return recognition light LRr having a return recognition spectrum.

The interaction of the incident recognition light LRi with the marking portion of the marked or unmarked container, which results in the return recognition light LRr may include, for example, an interaction by reflection on a surface of the marked or free marking portion, or an interaction by a transmission through the constituent material of the marking portion, possibly including the constituent material of the control mark. As will be seen below, the interaction may include a luminescence phenomenon in which the incident recognition light LRi is at least partly absorbed by the control mark, and wherein, due to this absorption, the material of the control mark emits a return recognition light, LRr including a light emitted by the luminescent material. In the course of this interaction, the light may undergo various modifications such as refraction, reflection, spectrum modification, diffusion, etc., which transform the incident recognition light LRi into return recognition light LRr.

For collecting a return recognition light, the recognition facility may optionally include an optical collector collecting the return recognition light resulting from the interaction of the incident recognition light with the marking portion, and optionally with the control mark, of a container, the marking portion of which is placed in the recognition area of the facility. In the illustrated example, the recognition optical collector comprises an objective 36 belonging to a recognition camera 38. Preferably the objective 36 can be used to produce an image of the marking portion which preserves the topology of an optional pattern of the control mark and therefore, if need be, preserves the identification information optionally borne by the pattern of the mark, in the optical image.

The optical recognition procedure may convert, in a recognition spectral band, the collected return recognition light LRr into a linear or two-dimensional multipoint recognition digital image. The recognition spectral band is the set of wavelengths of a light that may be converted into a recognition digital image IR. This is a feature of the conversion, and optionally of the collection of the return light, and notably of the means implemented for ensuring this conversion, and optionally of the means implemented for this collection. The recognition spectral band may include the entirety of the return recognition spectrum, in which case the entirety of the light information contained in the return recognition light is converted into the recognition digital image. The recognition spectral band may only intersect a part of the return recognition spectrum, in which case only the light information contained in this part of the return recognition spectrum is used for forming the recognition digital image. Conversely, the return recognition spectrum may only include a part of the recognition spectral band.

Typically, for this conversion operation, a linear or two-dimensional recognition photoelectric sensor is used, e.g. the sensor of a recognition camera 38. Typically, the optical collector forms, on a sensitive surface of the photoelectric sensor, the stigmatic optical image of the marking portion of the container. The sensitive surface of the photoelectric sensor comprises, for example, one or more series of photoreceptor elements, notably juxtaposed photoelectric elements, in the case of a two-dimensional sensor, along a grid with perpendicular rows and columns. The recognition photoelectric sensor may be of the same technology as the inspection photoelectric sensor, or of different technology. The recognition photoelectric sensor converts, in the recognition spectral band, the collected return recognition light LRr into a linear or two-dimensional multipoint recognition digital image IR, composed of pixels. The recognition digital image IR then corresponds to the stigmatic optical image of the marking portion of the container which is formed on the sensitive surface of the sensor by the light collector.

As explained above regarding the inspection spectral band, the recognition spectral band notably depends on the sensitivity wavelength range of the recognition sensor and may also be adapted by the presence of spectral filters in the recognition optical collector. The recognition spectral band is therefore a feature of the recognition sensor and of the recognition collector. In the embodiment, it is therefore a feature of the recognition camera 38.

Preferably the recognition digital image IR comprises at least 128 pixels.

As described above regarding the inspection procedure, the recognition procedure may produce a unique recognition digital image IR for a given container, or a series of recognition digital images of a given container.

The analysis of recognition digital images is generally performed by computer by a computer unit 30 configured for recognizing a possible control mark on a control container. Such a computer unit 30 may be a dedicated unit, or be common with another optical facility, notably an inspection optical facility 16a, 16b or with other line facilities as explained above.

In the implementation of the method of checking, provision may be made for analyzing the recognition digital image for recognizing the control mark possibly present on the container, which is located in the recognition area, according to image analysis techniques known to the person skilled in the art, e.g. similar to the techniques described above concerning the inspection procedure.

The computer analysis of recognition digital images produces a recognition result that may include a binary result (true/false, present/absent, compliant/non-compliant, control/no control, etc.). In this case, the container is simply identified, for example, as being a control container, by detecting the mark, without discriminating with regard to a particular characteristic of the container. In some cases, the recognition procedure makes it possible to uniquely identify the control container or as belonging to a determined category of control containers from among a plurality of distinct categories of control containers, by detection and recognition of the mark. The recognition of the mark may be based on the recognition of the geometry or of a pattern of the mark. It may also be based on the recognition of a particular spectral transformation of the incident light by interaction with the mark. The determined category of control containers is, for example, the set of control containers associated with the same distinct expected inspection result, e.g. having the same known physical characteristic, from among a plurality of distinct categories of control containers, each associated with a distinct expected result, e.g. having at least one distinct known physical characteristic for each category. Thus, a category is, for example: "controls without defect", "controls too high", "controls with crack in the ring". If the identifier is unique for each control, the known characteristic may be a measurement value, e.g. "height=252 mm".

Preferably the computer unit comprises a means of storing the correspondence relationships between identifiers of control marks and expected inspection results for control containers bearing said control marks. Thus, identifiers are associated in memory with categories or measurement values. A simple implementation consists in entering information in correspondence tables in the memory of the computer processing unit.

Preferably, the control mark has at least one detectable known characteristic in the recognition digital image, more preferably, a combination of detectable known characteristics in the recognition image.

Preferably, the control mark affixed to the marking portion of a control container, has optical properties of spectral transformation that confer on the marked marking portion optical properties of spectral transformation which:

for the recognition procedure, differ from those of the free marking portion in a useful portion of the incident recognition spectrum and/or a useful portion of the recognition spectral band;

for the inspection procedure, are identical to those of the free marking portion in the whole of the useful portion of the incident inspection spectrum and in the whole of the useful portion of the inspection spectral band.

The useful portion respectively of the incident inspection or recognition spectrum or spectral band, are respectively the subset of the wavelengths of the incident spectrum or spectral band which are actually used for obtaining the light information contained in the corresponding digital image for the needs of the corresponding procedure.

Thus, the useful portion of the incident inspection (respectively recognition) spectrum is that which produces, after interaction with the inspected portion (respectively with the marking portion) of the container, a return inspection (respectively recognition) light in the inspection (respectively recognition) spectral band.

The useful portion of the inspection (respectively recognition) spectral band, is the portion of the spectral band which intersects the return inspection (respectively return recognition) spectrum. For a given inspection or recognition spectral band, its useful part depends notably on the corresponding incident spectrum and the spectral transformation that is caused on this incident spectrum by interaction with the marked and/or free marking portion.

For example, in the case of an inspection procedure in which the inspection spectral band is limited to the infrared, the useful portion of the incident inspection spectrum is the one that produces, after interaction with the inspected part of the container, the portion of return inspection light, the spectrum of which lies in the infrared domain. According to another example, in the case of a recognition procedure in which the incident recognition spectrum produces, after interaction with the marking portion, a return recognition light, the spectrum of which lies in a domain limited, for example, to the blue domain, the useful portion of the recognition spectral band is the one that intersects the return recognition spectrum, namely the blue domain.

The optical properties of spectral transformation consist, for example, of the optional faculty of modifying, therefore of transforming, the spectral intensity distribution of an incident light.

In the present document, the optical properties of spectral transformation of a material refer to the way in which a material interacts with light, this interaction being considered according to the wavelengths, so that if the interaction has different consequences for different wavelengths, the spectral intensity distribution contained in the light is modified, and therefore transformed, if the incident light and the return light resulting from the interaction of the incident light with the material are compared. The spectral transformation generally includes a partial or complete absorption of certain wavelengths of the incident light. It may also include, e.g. In the case of a photoluminescent material, an addition or a reinforcement of certain wavelengths in the return spectrum with respect to the incident spectrum. In a modifying transformation, the spectrum, in the sense of the set of wavelengths present with a non-zero intensity in a light, may be unchanged, with only a modification of the spectral intensity distribution of these wavelengths. A neutral transformation of the spectral intensity distribution contained in a light corresponds to the case where the spectral intensity distribution contained in the light is not modified in the spectral band considered.

Advantageously, such properties of the control mark lead to the control mark being detectable in the recognition digital image obtained in the recognition procedure, e.g. obtained by means of the recognition sensor, when the control mark is illuminated by the recognition light source, but not detectable in the inspection digital image obtained in the inspection procedure, e.g. obtained by the inspection photoelectric sensor when the control mark is illuminated by the inspection light source.

A control mark may be considered as detectable in the recognition digital image if the pixels in the image are separable from the image pixels of the background on which it appears, notably if the photometric characteristics of the pixels in the image, e.g. in terms of grayscale, color and/or contrast, differ, locally or globally, from the photometric characteristics of the image pixels of the free marking portion, therefore of the background, with a difference in detection allowing a sufficient degree of confidence. For example, the difference in grayscale between the image pixels of the mark and the image pixels of the background is at least greater than the electronic noise of the image. These different photometric characteristics make it possible to optionally express a texture and/or a shape or a combination of these factors, which differ from the texture and/or shape or combination possibly present in a container without a control mark.

Conversely, a mark is considered as non-detectable in the inspection digital image when, in the inspection image, the pixels in the image are not separable from the those of the background on which it appears, i.e., for example, they display a level of light, color and/or contrast that differ from those of the background, and therefore of the free marking portion, only by a difference close to or below the noise level.

The background of a digital image may be considered as being the digital image of the same portion, notably of the marking portion, of an identical container lacking any control mark.

The implementation of a method according to the invention, or the use of a system according to the invention, will be particularly advantageous when the marking portion of a control container at least partly intersects the inspected portion of the control container which is inspected in the inspection procedure. Indeed, in this case, the presence of the control mark on the inspected portion will not prevent the check from being able to be made since, during the implementation of the inspection procedure, the control mark may be considered undetectable.

In some embodiments, the optical properties of spectral transformation of the marked marking portion differ from those of the free marking portion in a part of the incident recognition spectrum that is not included in the incident inspection spectrum. This is a means of allowing the control mark to be detectable in the recognition digital image.

In some embodiments, the optical properties of spectral transformation of the mark differ from those of the free marking portion so that, when they are illuminated by the incident recognition light, the corresponding return recognition lights for the mark and for the free marking portion are different in the recognition spectral band. This is another means of allowing the control mark to be detectable in the recognition digital image.

Furthermore, the optical properties of spectral transformation of the control mark are preferably such that, when it is illuminated by the incident inspection light, the return inspection lights for the marked marking portion and for the free marking portion are identical in the inspection spectral band, at least in its useful portion. This is a means for allowing the control mark not to be detectable in the inspection digital image.

The difference between the optical properties of spectral transformation of the marked marking portion and those of the free marking portion are considered here as at least partly resulting from the presence of the control mark on the marking portion, preferably resulting exclusively from the presence of the control mark on the marking portion.

The optical properties of spectral transformation of the control mark may cause a transformation between the spectral intensity distribution of the incident recognition, respectively inspection, light and the spectral intensity distribution of the return recognition, respectively inspection, light resulting from the interaction of the incident recognition, respectively inspection, light with the marked marking portion. Similarly, the optical properties of spectral transformation of the free marking portion may cause a transformation between the spectral intensity distribution of the incident recognition, respectively inspection, light and the spectral intensity distribution of the return recognition, respectively inspection, light resulting from the interaction of the incident recognition, respectively inspection, light with the free marking portion. According to circumstances, these modifications may be modifying transformations, or neutral transformations.

The difference between the optical properties of spectral transformation of the mark and those of the free marking portion may therefore lead to the difference between transformations undergone by an incident light by interaction respectively with the marked marking portion and the free marking portion.

A modifying transformation between the spectral intensity distribution of an incident light and the spectral intensity distribution of the return light resulting from the interaction of the incident light with either the free marking portion, or with the marked marking portion, may include the absorption, reflection, diffraction and/or refraction of a control spectral band. It may include a phenomenon of photoluminescence, notably fluorescence, with, for example, total or partial absorption of an excitation spectral band, and/or emission of a luminescence spectrum.

A modifying transformation of the spectral intensity distribution of a light on a considered spectrum means that the intensity values of its wavelength components are modified over at least one part of the extent of the considered spectrum.

Two modifying transformations differ over a given spectrum or a given spectral band notably if the modifications of the intensity values are different over at least one part of the spectrum or the spectral band considered.

In some embodiments, the optical properties of spectral transformation of the marked marking portion are such that:
  the interaction of the recognition light with the marked marking portion causes a modifying recognition transformation between the spectral intensity distribution of the incident recognition light and the spectral intensity distribution of the return recognition light, and
  the interaction of the recognition light with the free marking portion causes a neutral or modifying non-recognition transformation, between the spectral distribution of the incident recognition light and the spectral distribution of the return recognition light, and
  the recognition transformation differs from the non-recognition transformation of the recognition spectral band, notably at least in one part of its useful portion.

Notably for such an embodiment, the interaction of the inspection light with the marked marking portion and with the free marking portion cause the same neutral or modifying inspection transformation, between the spectral intensity distribution of the incident Inspection light and the spectral intensity distribution of the return inspection light in the inspection spectral band, notably at least in the whole of its useful portion. In other words, both transformations do not differ in the inspection spectral band, in any case not in its useful portion.

In a first category of embodiment, it is provided that the interaction of the incident recognition light with the control mark causes a modifying transformation, at least in the recognition spectral band, between the spectral intensity distribution of the incident recognition light and the spectral intensity distribution of the return recognition light.

This makes it possible to ensure that the control mark is detectable by the recognition sensor when it is illuminated by the incident recognition light.

In parallel with this, it is provided that the interaction of the incident inspection light with the control mark of the container causes a neutral transformation, at least in the useful part of the inspection spectral band, between the spectral distribution of the incident recognition light and the spectral distribution of the return recognition light. Neutral transformation in a considered spectral band, is understood to mean that it does not create any modifying transformation of the spectral intensity distribution that is detectable in the considered spectral band. Such a neutral transformation is found, for example, in the case of a transmission through a non-absorbent or "transparent" material in a considered spectral band. Thus, here, the incident inspection light is not modified over the extent of the inspection spectral band, in any case at least in its useful portion, by interaction with the control mark.

This makes it possible to ensure that the control mark is not detectable by the inspection sensor when it is illuminated by the incident inspection light.

In other words, the control mark is only detectable when it is illuminated with the incident recognition light, and not when it is illuminated with the inspection light. For this, the control mark interacts with the incident recognition light in a different way from the way in which it interacts with the incident inspection light. This difference in interaction is expressed at least in the recognition spectral band, but not in the inspection spectral band, in any case in its useful part. In the inspection spectral band, the control mark does not modify the spectral intensity distribution of the incident inspection light.

A first embodiment belonging to this first category of embodiments involves the use of a control mark comprising a photoluminescent material.

A photoluminescent material is a material which, under the effect of an illumination in an excitation spectral band, emits a luminescence light which exhibits a luminescence spectrum.

In such an embodiment provision will be made that the incident recognition spectrum comprises at least one part of the excitation spectral band, so that the recognition light actually excites the luminescent material, while the incident inspection spectrum is disjoint from the excitation spectral band so that the inspection light does not actually excite the luminescent material and does not cause the luminescence phenomenon. In this case, the visibility or non-visibility of the control mark is controlled by switching on either the recognition light source or the inspection light source.

Thus, the feature referred to above is found, according to which the interaction of the recognition light with the control mark causes a modifying transformation in the recognition spectral band. The interaction of the inspection light with the control mark does not cause this transformation in the inspection spectral band, in any case not in the useful part of the inspection spectral band.

For this, the photoluminescent material is preferably transparent when illuminated with the incident inspection light, in the useful inspection spectral band.

Through the photoluminescence of the control mark, a marked marking portion is obtained that has optical properties of spectral transformation which
 for the recognition procedure, differ from those of the free marking portion in a useful portion of the incident recognition spectrum, in this case more specifically in the excitation spectral band;
 for the inspection procedure, are identical to those of the free marking portion in the whole of the incident inspection spectrum which does not include the excitation spectral band.

Of course, the luminescence spectrum and the recognition spectral band are chosen so that the luminescence spectrum is at least partially included in the recognition spectral band so that the luminescence light emitted by the control mark is detectable by the procedure and the recognition facility when the control mark is illuminated with the incident recognition light source including the excitation spectral band. In this case, it may equally be provided that the luminescence spectrum is at least partially included in the inspection spectral band, and that on the contrary, the luminescence spectrum is disjoint from the inspection spectral band.

For example, a luminescent material may be chosen, the excitation spectral band of which has a maximum wavelength less than 400 nm while the incident inspection spectrum has a minimum wavelength greater than 400 nm.

Such a material may therefore be excited by an incident recognition light containing ultraviolet. By choosing instead a source of inspection light, the spectrum of which does not comprise ultraviolet, or In any case not wavelengths in the excitation spectral band, e.g. an ordinary visible light (optionally filtered with an anti-UV filter), the differentiated interaction of the control mark with the incident recognition light is created, which makes the mark detectable, with respect to the incident inspection light, which does not make the control mark detectable by not triggering luminescence.

Advantageously, luminescent materials generally have an easy-to-detect luminescence spectrum, since they exhibit an easily recognizable peak in the spectral intensity distribution. This luminescence spectrum may be partially or completely included in the visible domain. In this case, a quite conventional sensor may be used as a recognition sensor. It will be noted that the return recognition light may optionally be filtered so as to only keep a part of this light including the expected part in the domain of the luminescence spectrum, and thus facilitate the detection of the control mark.

An example of a material that it is possible to use for forming a control mark in a procedure according to the invention is the material "Glass'in"® marketed by Athéor S.A.S., 104 rue de la Galéra, 34090 Montpellier, France. Such a material, which comes in the form of a liquid ink, is particularly suitable insofar as it is deposited on the glass by an ink jet printing technology, and it is capable of being transposed onto the glass in a particularly reliable and robust way via a simple ultraviolet process.

It is advantageous to provide, as with the material above, that the luminescence spectrum is partially or completely included in the visible domain. A control mark produced with such a material then proves perfectly detectable, even to the naked eye, when it is exposed to a light comprising ultraviolet, the material emitting, for example, a yellow/green light in the visible domain, that is perfectly detectable by conventional sensors or by the human eye. Conversely, when this material is illuminated with a light not significantly comprising any ultraviolet, a control mark formed using this material is undetectable by a conventional sensor.

In this embodiment, it is understood therefore that the inspection spectral band and the recognition spectral band may partially or completely coincide. Accordingly, two sensors of the same type may be used as a recognition sensor and as an inspection sensor, e.g. two conventional sensors operating essentially in the visible domain, or even a single sensor common to the two inspection and recognition facilities.

If two distinct sensors are used for the inspection facility and the recognition facility, these two facilities may be arranged on the line so as to correspond to distinct positions of the container. This is the arrangement that is illustrated in FIG. 1.

However, even in the case where two distinct sensors are used, it is possible to arrange the two inspection and recognition facilities in such a way that they observe a given container for the same position of the container along the conveying path on the line. It will be noted in this case that, even if a given container is observed for the same position along the conveying path both by the inspection facility and by the recognition facility, the inspection area and the recognition area may coincide or be disjoint, notably if the marking portion of the container is disjoint from the inspected portion of this container.

If a single common sensor is used for the inspection and recognition facilities, and in the more general case where the inspection spectral band and the recognition spectral band coincide or at least partially coincide and where the recognition facility and the inspection facility are arranged for observing a given container for the same position along the conveying path, it will advantageously be provided that the implementation of the inspection procedure and that of the recognition procedure are staggered over time. This staggering over time may result from alternately illuminating the container firstly by the incident inspection light and secondly by the incident recognition light.

In the case of the use of a luminescent material, the excitation spectral band of which is disjoint from the incident inspection spectrum, it may be enough to see to it that the incident recognition light is switched off during the implementation of the inspection procedure. On the other hand, at least in some cases, it is possible to keep the incident inspection light switched on during the implementation of the recognition procedure.

FIG. 3A illustrates what happens in a recognition procedure, for an embodiment involving a photoluminescent control mark. An incident recognition light LRi, having a spectral intensity distribution DSRi, illuminates a control container 12t provided with a control mark 42 on the marking portion 40. In the example, the recognition spectrum of the incident recognition light LRi is in the UV domain.

By interaction with the free marking portion 46, therefore without interaction with the control mark 42, the incident recognition light LRi becomes the return recognition light LRrl having a spectral intensity distribution DSRrl seen by the recognition sensor. The interaction with the free marking portion 46 is, for example, a simple reflection that does not modify the spectral intensity distribution. DSRri and DSRrl are therefore, for example, identical, the result of a neutral transformation.

By interaction with the marked marking portion 44, therefore with the control mark 42, the same incident recognition light LRi becomes the return recognition light LRrm having a spectral intensity distribution DSRrm. Due to the presence of the mark 42, here of its photoluminescence properties, the spectral intensity distribution DSRrm results from a modifying transformation, e.g. by absorption of the excitation spectral band and by the emission of the luminescence spectrum which lies, for example, in the visible domain.

It can be seen that the spectral intensity distributions DSRrl and DSRrm of the return recognition lights resulting from these two interactions, with the free marking portion and with the marked marking portion respectively, are different.

In the illustrated example, for forming a recognition digital image, a recognition sensor is used, the recognition spectral band BSR of which corresponds, for example, to the visible domain.

For the image pixels corresponding to the free marking portion 46, this sensor cannot convert the return recognition light LRrl, in the UV domain, which is expressed by a spectral intensity distribution DSCRl actually converted in the image without any wavelength for these pixels. The corresponding pixels are therefore black pixels in the recognition digital image.

For the image pixels corresponding to the marked marking portion 44, this sensor may on the contrary convert a return recognition light LRrm, in the visible domain, which is expressed by a spectral intensity distribution DSCRm actually converted in the image. The corresponding pixels are therefore light pixels in the recognition digital image. In this example, the useful portion of the recognition spectral band is therefore the set of wavelengths for which the intensity is not zero in the spectral intensity distribution DSCRm actually converted in the image.

The spectral intensity distributions DSCRl and DSCRm actually converted in the image, for the free portion and for the marked marking portion respectively, are therefore different. Clearly therefore it is possible to recognize the presence of the mark in the recognition image.

FIG. 3B illustrates what happens in an inspection procedure, for the same embodiment. An incident inspection light LIi, having a spectral intensity distribution DSIi, illuminates the same control container 12t. In the example, the inspection spectrum of the incident inspection light LIi is in the visible domain.

By interaction with the free marking portion 46, therefore without interaction with the control mark 42, the incident inspection light LIi becomes the return inspection light LIrl having a spectral intensity distribution DSIrl seen by the inspection sensor. The interaction with the free marking portion 46 is, for example, a simple reflection that does not modify the spectral intensity distribution. DSIi and DSIrl are therefore, for example, identical, the result of a neutral transformation.

By interaction with the marked marking portion 44, therefore with the control mark 42, the same inspection light LIi becomes the return inspection light LIrm having a spectral intensity distribution DSIrm. The mark 42, although photoluminescent, is assumed to have the same properties in the visible domain as those of the underlying glass forming the marking portion, or else have been deposited in a very thin layer not modifying the visible light. Luminescence does not occur since the visible spectrum LIi does not contain the excitation wavelengths. DSRi and DSIrm are therefore, for example, identical, the result of a neutral transformation.

In this case, the spectral intensity distributions DSIrl and DSIrm of the return inspection lights resulting from these two interactions are identical.

In the illustrated example, for forming an inspection digital image, an inspection sensor is used, the inspection spectral band BSI of which corresponds to the visible domain.

Both for the image pixels corresponding to the free marking portion 46, and for the image pixels corresponding to the marked marking portion 44, this sensor converts the return inspection light Lrl and LIrm into light pixels in the inspection digital image. The spectral intensity distributions DSCRl and DSCRm actually converted in the image, for the free marking portion and for the marked marking portion respectively, are identical. Clearly therefore it is not possible to detect the presence of the mark 42 in the inspection image.

On the other hand, if the marking portion 40 contains a defect, the interaction of the defect with the inspection light would be identical whether the defect is located in the marked part or in the free part, so that it would be detectable by the inspection procedure, regardless of the presence or absence of the control mark.

In this example, the useful portion of the inspection spectral band is therefore the set of wavelengths for which the intensity is not zero in the spectral intensity distribution DSCIl, DSCIm actually converted in the image, which is here limited by the spectral intensity distribution DSIi of the incident inspection light LIi. The useful portion of the incident inspection spectrum corresponds to the set of wavelengths of the spectral intensity distribution DSIi of the incident inspection light LIi, since they are all found in the spectral intensity distribution DSCIl, DSCIm actually converted in the image.

Still in the context where the incident inspection spectrum is different from the incident recognition spectrum, this spectral difference in the incident lights may be exploited by providing that the control mark absorbs a control spectral band which is included in the incident recognition spectrum of the incident recognition light, but which is not included in the incident inspection spectrum of the incident inspection light. On the contrary, the control mark will be preferably "non-absorbent" or with almost zero absorbance, in other words "transparent" in its interaction with the incident inspection light, in the inspection spectral band, in any case in its useful portion.

In this case, it will be advantageously provided that the recognition spectral band includes the return recognition spectrum.

For example, the inspection procedure may use a red incident inspection source, the incident inspection spectrum of which extends, by way of illustration, between 650 and 750 nanometers. The inspection spectral band may, for example, cover the whole of the visible domain ranging from 400 to 780 nm, but it could be narrower. The control mark may comprise a material that absorbs a certain control spectral band, e.g. a spectral band in the blue domain, e.g. the control spectral band ranging from 450 to 500 nm, while preferably not absorbing outside, notably in the useful portion of the inspection spectral band. In these circumstances, a recognition spectral band will be chosen that includes at least one part of the control spectral band, preferably the whole of the control spectral band. In this case, the recognition spectral band may cover the blue domain ranging from 450 to 500 nm. However, it may also be provided that the recognition spectral band covers the whole of the visible domain. Clearly, in these circumstances, a control sample will be recognized as such by the recognition procedure since the control mark will appear, in the recognition procedure, as dark, or even black, and will thus be able to be detected, or even recognized. On the other hand, in the inspection procedure, as the incident inspection light does not comprise the control band, the presence of this control mark will be not detectable, so that the control mark will not hinder the inspection.

It is noted that a photoluminescent material is generally a material that absorbs the wavelengths of its excitation spectral band, which may be turned to advantage for the recognition procedure in the case where the excitation spectral band intersects the recognition spectral band, notably as a supplement to the detection of the luminescence spectrum. The excitation spectral band may then be considered as a control spectral band absorbed by the photoluminescent material.

In some embodiments a mark may be used diverting only the useful portion of the incident recognition light, such that the diversion prevents this useful portion from being seen by the recognition sensor, through the recognition optical collector, but it does not divert the incident inspection light, in the useful portion of the inspection band. A dichroic surface treatment of the glass (or an ink), capable of reflecting certain wavelengths and transmitting other wavelengths in the glass makes it possible to perform such a marking.

In other embodiments, the control mark affixed to the marking portion of a control container has optical properties of spectral transformation that confer on the marked marking portion optical properties of spectral transformation which:

for the recognition procedure, differ from those of the free marking portion in the recognition spectral band, notably at least in its useful portion;

for the inspection procedure, are identical to those of the free marking portion in the inspection spectral band, in any case in the whole of its useful portion.

Here, as an alternative to, or supplementary to the exploitation of a difference between the incident inspection spectrum and the incident recognition spectrum, a difference is exploited between the recognition spectral band and the inspection spectral band.

In this case, it will be advantageously provided that the recognition spectral band includes a useful portion which is distinct, or even preferably disjoint, from the spectral band, in any case from its useful portion. In other words, the recognition spectral band then includes at least one part of its useful portion, or even preferably the entirety of its useful portion, which is not included in the inspection spectral band.

The disjunction between the inspection and recognition spectral bands may be obtained either by using different types of sensors having spectral bands of different sensitivity, and/or by providing in front of one or the other of the sensors, or in front of both, filters blocking certain wavelengths so as to ensure the disjunction.

For example, it may be ensured that one of the inspection or recognition spectral bands, extends substantially in the infrared domain, while the other of the two spectral bands could, for example, be limited to the visible and/or ultraviolet domain, or in any case exclude the infrared domain.

In other words, in such embodiments, the recognition procedure and the inspection procedure analyze different parts of the optical spectrum.

In this case, it is preferably provided that the interaction of the control mark with the incident inspection light does not cause any modifying transformation of the incident inspection light in the inspection spectral band, in any case in the useful part of the inspection spectral band. In other words, the control mark is transparent in its interaction with the incident inspection light, in the inspection spectral band, in any case in the useful part of the inspection spectral band.

In a variant, a photoluminescent material may be chosen, the luminescence spectrum of which is disjoint from the inspection spectral band, in any case disjoint from the useful part of the inspection spectral band.

According to another variant, it may be provided, for example, that the control mark absorbs a control spectral band which is included in the recognition spectral band, and which is not included in the inspection spectral band, in any case not included in the useful part of the inspection spectral band.

One embodiment may consist in the production of a control mark with a material that absorbs a certain control spectral band, e.g. a spectral band in the blue domain, e.g. the control spectral band ranging from 450 to 500 nm, but transparent outside.

In this case, it will be provided that the recognition spectral band contains at least one part of the control spectral band. It may optionally be chosen to limit the recognition spectral band so that it contains the control spectral band absorbed by the control mark, or even coincide with the control spectral band, but that it is, for example, disjoint, or in any case distinct, therefore with a disjoint part, from the inspection spectral band. Here again, if it is wanted to limit the recognition spectral band, this may be achieved by placing, in front of a conventional sensor used for the recognition procedure, a spectral filter allowing only a part of the optical band to pass, e.g. a disjoint part of the inspection spectral band. Such a filter may, for example, cut out all the wavelengths above 600 nm, or even all the wavelengths above 500 nm. This will make it possible to increase the contrast with which the mark will be seen in the recognition image.

The absorbent nature of the control mark ensures that the interaction of the recognition light with the control mark causes a modifying transformation in the recognition spectral band.

In this case, it may be chosen to perform the inspection procedure in an inspection spectral band disjoint from the control spectral band blocked by the material of the control mark, e.g. a domain, the lower wavelength limit of which is 600 nm or even 780 nm for limiting the inspection spectral band to the infrared domain. The interaction of the inspection light with the control mark of the container causes a neutral transformation, at least in the inspection spectral band, between the spectral distribution of the incident inspection light and the spectral distribution of the return inspection light. This neutral transformation means that the spectral intensity distribution is not modified between the incident inspection light and the return inspection light, at least in the inspection spectral band. The incident inspection light is therefore preferably chosen so that its interaction with the material of the free marking portion of the container results in a return inspection light which is mostly included in the inspection spectral band. For example, if the inspection spectral band is limited to the infrared domain, it may be provided to use a source of incident inspection light in the infrared domain.

It will be noted that for the inspection procedure, it is possible to use an incident inspection light which includes the control spectral band, but preferably an incident inspection light will be used which does not include the control spectral band.

For the recognition procedure, it may then be provided to illuminate the container with an incident recognition light comprising a component in the control spectral band absorbed by the material of the control mark. Preferably, the major part of the luminous intensity of the recognition light will be located in the control spectral band absorbed by the material of the control mark. Thus, in the absence of the control mark, a significant luminosity will be detected in the recognition procedure in the free marking portion of the container. In the presence of the control mark, the recognition procedure will only see a weak luminosity or even no luminosity for the marked marking portion. Thus, the control mark will appear dark, or even black, therefore with a high contrast, and it will be possible to easily recognize it in an analysis step by implementing an image processing process well known to the person skilled in the art.

Another example will now be described where the recognition spectral band and the inspection spectral band do not coincide, more particularly where the recognition spectral band includes a portion which is not included in the inspection spectral band, and where the presence of the control mark is detectable under the effect of the recognition light, only in a part of the optical spectrum that is included in the recognition spectral band, but not in the inspection spectral band.

For this, provision may be made, for example, that the control mark absorbs a control spectral band which is included in the detection spectral band and which is not included in the inspection spectral band. As in a previous example, the control mark may comprise a material that absorbs a control spectral band in the blue domain ranging from 450 to 500 nm. To facilitate understanding, the example is used of a recognition procedure and an inspection procedure by reflection.

For example, the inspection procedure uses a red incident inspection source, the incident inspection spectrum of which extends, by way of illustration, between 650 and 750 nanometers in a spectrum where the control mark is transparent and colorless. However, the incident inspection source may also comprise a light, the spectrum of which extends over the whole of the visible domain. In this case, the inspection spectral band may be limited, for example, to a red band included, for example, between 650 and 750 meters. In these circumstances, a recognition spectral band will be chosen that includes at least one part of the control spectral band, preferably the whole of the control spectral band. In this case, the recognition spectral band may cover the blue domain ranging from 450 to 500 nm. However, it may also be provided that the recognition spectral band covers the whole of the visible domain. In the latter case, it is noted that it intersects the inspection spectral band, or even that it contains it entirely.

Similarly, the incident recognition spectrum must comprise at least the control spectral band but it may be more extended and may, for example, cover the whole of the visible domain, e.g. a white light. Clearly, in these circumstances, a control sample will be recognized as such by the recognition procedure since the control mark will appear in the recognition procedure. The control mark will appear even better when the recognition spectral band is limited. It is thus advantageous to limit the recognition spectral band to the control spectral band. On the other hand, in the inspection procedure, as the inspection spectral band does not comprise the control band, the inspection procedure will not distinguish between the presence of the mark and the absence of the mark. In this way, the presence of this control mark will not be visible, so that the control mark will not hinder the inspection.

It is noted that in this case, sources having the same spectrum may be used as an inspection light source and a recognition light source, optionally using one and the same source.

FIG. 4A illustrates what happens in a recognition procedure, for an embodiment involving a control mark absorbing at least one part of the incident recognition spectrum, e.g. a control spectral band corresponding to the blue part of the visible domain. An incident recognition light LRi, having a spectral intensity distribution DSRi, Illuminates a control container 12t provided with a control mark 42 on the marking portion 40. In the example, the incident recognition spectrum of the incident recognition light LRi extends over the whole visible domain. It is, for example, a white light.

By interaction with the free marking portion 46, therefore without interaction with the control mark 42, the incident recognition light LRi becomes the return recognition light LRrl seen by the recognition sensor and having a spectral intensity distribution DSRrl. The interaction with the free marking portion 46 is, for example, a simple reflection that does not modify the spectral intensity distribution. DSRi and DSRrl are therefore, for example, identical, the result of a neutral transformation, but not necessarily so.

By interaction with the marked marking portion 44, therefore with the control mark 42, the same incident recognition light LRi becomes the return recognition light LRrm having a spectral intensity distribution DSRrm. Due to the presence of the mark 42, here of its absorption properties, the spectral intensity distribution DSRrm is the result of a modifying transformation, e.g. by absorption of the control spectral band. Here the case is illustrated of a mark absorbing the blue part of the visible domain.

It can be seen that the spectral intensity distributions DSRrl and DSRrm of the return recognition lights resulting from these two interactions, with the free marking portion and with the marked marking portion respectively, are different in the blue part of the spectrum and identical in its red part.

In the illustrated example, for forming a recognition digital image, a recognition sensor is used, the recognition spectral band BSR of which corresponds to the blue part of the visible domain. This may be achieved by filtering the other parts of the visible domain.

For the image pixels corresponding to the free marking portion 46, this sensor can only convert the part of the return recognition light LRrl, located in the blue part of the visible domain, which is expressed by a spectral intensity distribution DSCRl actually converted in the image having a luminosity in the blue. The corresponding pixels are therefore light pixels in the recognition digital image.

For the image pixels corresponding to the marked marking portion 44, this sensor cannot, on the contrary, convert the return recognition light LRrm, since it does not comprise wavelengths in the blue part of the visible domain, which is expressed by a spectral intensity distribution DSCRm actually converted in the image without non-zero intensity wavelengths. The corresponding pixels are therefore black pixels in the recognition digital image.

In this example, the useful portion of the recognition spectral band is therefore the entirety of the recognition spectral band. On the other hand, the useful part of the incident recognition spectrum is limited to the part of this spectrum that is actually converted by the sensor, therefore limited to the recognition spectral band since, in this example, the latter is entirely included in the incident recognition spectrum.

The spectral intensity distributions DSCRl and DSCRm actually converted in the image, for the free portion and for the marked marking portion respectively, are therefore different. It can be seen therefore that it is possible, in the recognition image, to detect the presence of the mark, or even to recognize the mark, which appears here in black on a light background.

FIG. 4B illustrates what happens in an inspection procedure, for the same embodiment. An incident inspection light LIi, having a spectral intensity distribution DSIi, illuminates the same control container 12t. In the example, the inspection spectrum of the incident inspection light LIi is the same as that of the incident recognition light LRi.

By interaction with the free marking portion 46, therefore without interaction with the control mark 42, the incident inspection light LIi becomes the return inspection light LIrl having a spectral intensity distribution DSIrl seen by the inspection sensor. The interaction with the free marking portion 46 is, for example, a simple reflection that does not modify the spectral intensity distribution. The spectral intensity distributions DSIi and DSIrl are therefore, for example, identical, the result of a neutral transformation. The transformation could be modifying.

By interaction with the marked marking portion 44, therefore with the control mark 42, the same incident inspection light LIi becomes the return inspection light LIrm having a spectral intensity distribution DSIrm. The mark 42, having absorbed the blue part of the visible domain, has, on the other hand, the same properties in the rest of the visible domain, notably in the red area, as those of the underlying glass forming the marking portion. The spectral intensity distributions DSIi and DSIrm are therefore, for example, identical in the red domain, while being different in the blue domain.

In this case, the spectral intensity distributions DSIrl and DSIrm of the return inspection lights resulting from these two interactions are different in the blue domain, while being, for example, identical in the red domain, or being the result of an identical modifying transformation in the inspection spectral band, here in the red domain.

In the illustrated example, for forming an inspection digital image, an inspection sensor is used, the corresponding inspection spectral band BSI of which is, for example, limited to the red part of the visible domain.

Both for the image pixels corresponding to the free marking portion 46, and for the image pixels corresponding to the marked marking portion 44, this sensor converts the corresponding return inspection lights LIrl and LIrm into light pixels in the inspection digital image. Insofar as these two return inspection lights have, in the inspection spectral band, in any case in its useful part, the same spectral intensity distribution, the spectral intensity distributions DSCIl and DSCIm actually converted in the image, for the free marking portion and for the marked marking portion respectively, are identical. It can be seen therefore that it is not possible, in the inspection image, to detect the presence of the mark 42, despite the fact that the return inspection lights resulting from these two interactions are different in the blue domain. Indeed, the part of the spectrum in which they differ is outside the inspection spectral band, although the difference is not visible in the inspection digital image.

In this example, the useful portion of the recognition spectral band corresponds to the entirety of the inspection spectral band. It can be seen notably that the inspection spectral band is entirely included in the incident inspection spectrum. On the other hand, the useful portion of the incident inspection spectrum is limited to the set of wavelengths of the incidence spectral band, since the other wavelengths of the incident inspection spectrum are not converted by the inspection sensor.

As mentioned for some examples above, when the recognition spectral band includes a portion that is not included in the inspection spectral band, the invention may be implemented with a control mark comprising a photoluminescent material, the luminescence spectrum of which is included in the recognition spectral band but not in the inspection spectral band.

As is apparent from the examples above, it may advantageously be provided to exploit both a difference between the incident inspection spectrum and the incident recognition spectrum and a difference between the recognition spectral band and the inspection spectral band. In this case, the control mark, affixed to the marking portion of a control container, has optical properties of spectral transformation that confer on the marked marking portion optical properties of spectral transformation, which
- for the recognition procedure, differ from those of the free marking portion in a useful portion of the incident recognition spectrum and of the recognition spectral band;
- for the inspection procedure, are identical to those of the free marking portion in a useful portion of the incident inspection spectrum and of the inspection spectral band.

In many cases, it is provided that the inspection photoelectric sensor and the detection photoelectric sensor are distinct sensors, including in cases where the inspection spectral bands may coincide.

In some cases, e.g. if the recognition and inspection procedures are implemented for the same position of a given container on a conveying path, and more particularly in the cases where the inspection and recognition areas coincide, provision may be made that the recognition and inspection light sources are switched on alternately. This makes it possible to temporally separate the inspection procedure and the recognition procedure. In this case, they may be implemented using the same photoelectric sensor for inspection and recognition.

In some embodiments, the return recognition spectrum is disjoint from the inspection spectral band. Then the recognition and inspection procedures may be implemented simultaneously by providing that they are implemented for the same position of a given container on a conveying path.

When the mark is not visible to the human eye under the ambient lighting of the line, but becomes visible to the human eye under the effect of a particular incident light, e.g. when the mark is a photoluminescent ink emitting visible light under excitation by UV rays, an area of circulation on the line may advantageously be provided, lit by said particular incident light, in order that an operator may recover control containers which would be in circulation on the line, e.g. following a human error or a malfunction of an inspection or ejection facility.

The invention is not limited to the examples described and represented since various modifications may be applied thereto without departing from its scope.

The invention claimed is:

1. A method of checking a procedure for the optical inspection of glass containers (12), wherein the optical inspection procedure of a container comprises the steps of:
   illuminating at least one inspected portion of the container with an incident inspection light (LIi) having an incident inspection spectrum;
   collecting a return inspection light (LIrl, LIrl) resulting from the interaction of the incident inspection light (LIi) with the inspected portion of the container, the return inspection light having a return inspection spectrum;
   converting, in an inspection spectral band (BSI), the collected return inspection light (LIrl, LIrl) into a linear or two-dimensional multipoint inspection digital image (II);
   analyzing the inspection digital image (II) for determining an inspection result from the inspected container (12),
   wherein the method of checking comprises the steps of:
   inspecting, in accordance with the optical inspection procedure, a control container (12t) comprising a control mark (42) affixed to a marking portion of the control container (40);
   comparing an inspection result from the control container (12t) determined by the optical inspection procedure to a known inspection result from the control container (12t);
   characterized in that:
   the method of checking comprises a procedure for the optical recognition of a control container by optical reading of a control mark (42) in a marked marking portion (44) of the control container (12t), comprising the steps of:
      illuminating at least the marking portion (40) of the container with an incident recognition light (LRi) having an incident recognition spectrum;
      collecting a return recognition light (LRr) resulting from the interaction of the incident recognition light with the marking portion (40) and a possible control mark, the return recognition light (LRr) having a return recognition spectrum;
      converting, in a recognition spectral band (BSR), the collected return recognition light into a linear or two-dimensional multipoint recognition digital image (IR);
      analyzing the recognition digital image (IR) by computer for recognizing the possible control mark (42) therein;
   and in that the control mark (42), affixed to the marking portion of a control container, has optical properties of spectral transformation such that:
   the transformation of the spectral intensity distribution between the incident recognition light (LRi) and the return recognition light (LRr), caused by interaction with the marked marking portion (44), is different, inside at least the recognition spectral band (BSR), from a transformation of the spectral intensity distribution between the incident recognition light and the return recognition light, caused by interaction with a marking portion free of any mark (46);
   the transformation of the spectral intensity distribution between the incident inspection light (LIi) and the return inspection light (LIr), caused by interaction with the marked marking portion, is not different, inside at least one useful portion of the inspection spectral band (BSI), from the transformation of the spectral intensity distribution between the incident inspection light and the return inspection light by interaction with a marking portion free of any mark (46).

2. The method of checking according to claim 1, characterized in that the optical properties of spectral transformation of the marked marking portion (44) differ from those of the free marking portion (46) in a part of the incident recognition spectrum that is not included in the incident inspection spectrum.

3. The method of checking according to claim 1, characterized in that the optical properties of spectral transformation of the marked marking portion (44) differ from those of the free marking portion (46) so that, when they are illuminated by the incident recognition light (LRi), the corresponding return recognition lights for the marked marking portion (44, LRrm) and for the free marking portion (46, LRrl) are different in the recognition spectral band (BSR).

4. The method of checking according to claim 1, characterized in that the optical properties of spectral transformation of the control mark are such that, when they are illuminated by the incident inspection light, the return inspection light for the marked marking portion (44, LRrm) and the return inspection light for the free marking portion (46, LRrl) are identical in the useful portion of the inspection spectral band.

5. The method of checking according to claim 1, characterized in that the interaction of the inspection light with the marked marking portion (44) and with the free marking portion (46) cause the same neutral or modifying transformation, between the spectral intensity distribution (DSIi) of the incident inspection light (LIi) and the spectral intensity distribution (DSIrm, DSIrl) of the return inspection light (LIr) in the inspection spectral band.

6. The method of checking according to claim 1, characterized in that the control mark (42) comprises a photoluminescent material which, under the effect of an illumination in an excitation spectral band, emits a luminescence light which exhibits a luminescence spectrum, and in that the incident recognition spectrum comprises at least one part of the excitation spectral band while the incident inspection spectrum is disjoint from the excitation spectral band.

7. The method of checking according to claim 6, characterized in that the excitation spectral band of the luminescent material has a maximum wavelength less than 400 nm while the incident inspection spectrum has a minimum wavelength greater than 400 nm.

8. The method of checking according to claim 1, characterized in that the control mark (42) comprises a photoluminescent material which, under the effect of an illumination in an excitation spectral band, emits a luminescence light which exhibits a luminescence spectrum, and in that the luminescence spectrum is within the recognition spectral band (BSR) and disjoint from the inspection spectral band (BSI).

9. The method of checking according to claim 1, characterized in that the spectral inspection band (BSI) and the recognition spectral band (BSR) are disjoint, and in that the return inspection spectrum and the return recognition spectrum are disjoint.

10. The method of checking according to claim 1, characterized in that the incident inspection spectrum and the incident recognition spectrum are disjoint.

11. The method of checking according to claim 1, characterized in that the control mark (42) absorbs a control spectral band which is included in the recognition spectral band (BSR) and which is not included in the inspection spectral band (BSI).

12. The method of checking according to claim 1, characterized in that the control mark (42) absorbs a control spectral band which is included in the incident recognition light (LRi) and which is not included in the incident inspection light (LIi).

13. The method of checking according to claim 1, characterized in that the recognition procedure identifies the control container (12*t*) as belonging to a determined category of control containers from among a plurality of distinct categories of control containers.

14. The method of checking according to claim 1, characterized in that the recognition procedure uniquely identifies the control container (12*t*).

15. The method of checking according to claim 1, characterized in that the recognition procedure identifies the control container (12*t*) as belonging to a determined category of control containers, associated with the same expected inspection result.

16. The method of checking according to claim 1, characterized in that the marking portion (40) of a control container at least partly intersects the inspected portion of the control container (12*t*) which is inspected in the inspection procedure.

17. The method of checking according to claim 1, characterized in that it comprises the step of inserting at least one control container (12*t*) having an expected inspection result into a series of containers to be inspected (12) and checking that the inspection procedure determines the expected inspection result for said control container (12*t*).

* * * * *